United States Patent
Aballea et al.

(10) Patent No.: US 12,310,974 B1
(45) Date of Patent: May 27, 2025

(54) METHOD OF TREATING POST-TRAUMATIC STRESS DISORDER WITH CARPIPRAMINE

(71) Applicants: Samuel Aballea, Rotterdam (NL); Mondher Toumi, Luxembourg (LU)

(72) Inventors: Samuel Aballea, Rotterdam (NL); Mondher Toumi, Luxembourg (LU)

( * ) Notice: Subject to any disclaimer, the term of this patent is extended or adjusted under 35 U.S.C. 154(b) by 0 days.

(21) Appl. No.: 18/986,415

(22) Filed: Dec. 18, 2024

Related U.S. Application Data

(60) Provisional application No. 63/611,902, filed on Dec. 19, 2023.

(51) Int. Cl.
  *A61K 31/55* (2006.01)
  *A61P 25/00* (2006.01)

(52) U.S. Cl.
  CPC .............. *A61K 31/55* (2013.01); *A61P 25/00* (2018.01)

(58) Field of Classification Search
  CPC ....................................................... A61K 31/55
  See application file for complete search history.

(56) References Cited

U.S. PATENT DOCUMENTS

| | | |
|---|---|---|
| 4,956,362 A | 9/1990 | Goni et al. |
| 5,192,799 A | 3/1993 | Tomino et al. |
| 5,656,299 A | 8/1997 | Kino et al. |
| 11,123,311 B2 | 9/2021 | Hammock et al. |
| 11,298,363 B2 | 4/2022 | Baska et al. |
| 11,427,604 B2 | 8/2022 | Slassi et al. |
| 11,435,689 B2 | 9/2022 | Kawakami et al. |
| 11,591,353 B2 | 2/2023 | Slassi et al. |
| 11,597,738 B2 | 3/2023 | Slassi et al. |
| 2006/0193788 A1 | 8/2006 | Hale et al. |
| 2009/0318398 A1 | 12/2009 | Dudley et al. |
| 2011/0172188 A1 | 7/2011 | Mouthon et al. |
| 2015/0272946 A1 | 10/2015 | Sato et al. |
| 2016/0060702 A1 | 3/2016 | Li et al. |
| 2019/0008850 A1 | 1/2019 | Markovitz |
| 2019/0125696 A1 | 5/2019 | Hammock et al. |
| 2021/0228570 A1 | 7/2021 | Renger |

*Primary Examiner* — Yong S. Chong
(74) *Attorney, Agent, or Firm* — LESLEY A. WALLERSTEIN, LLC

(57) ABSTRACT

A method of treating Post-Traumatic Stress Disorder in a subject comprising administering a therapeutically effective amount of carpipramine or a pharmaceutically acceptable salt thereof.

11 Claims, No Drawings

METHOD OF TREATING POST-TRAUMATIC STRESS DISORDER WITH CARPIPRAMINE

CROSS REFERENCE TO RELATED APPLICATIONS

This application claims priority to U.S. Provisional Patent Application 63/611,902, filed Dec. 19, 2023.

FEDERALLY SPONSORED RESEARCH AND DEVELOPMENT

Not applicable.

FIELD OF THE INVENTION

This invention is directed to a method of treating post-traumatic stress disorder (PTSD) with carpipramine or a pharmaceutically acceptable salt thereof.

BACKGROUND OF THE INVENTION

Post-traumatic stress disorder (PTSD) is a psychiatric disorder that may occur in people who have experienced or witnessed a traumatic event such as a natural disaster, a serious accident, a terrorist act, war/combat, or rape or who have been threatened with death, sexual violence or serious injury.

The DSM-5 criteria for diagnosis of PTSD include: exposure to death, threatened death, actual or threatened serious injury, or actual or threatened sexual violence; presence of intrusion symptoms (persistent re-intrusion of traumatic event); avoidance of trauma-related stimuli after the trauma; negative alterations in cognition and mood; alterations in arousal and reactivity, these symptoms lasting for more than 1 month, symptoms creating distress or functional impairment.

Typical symptoms include depressed mood and loss of interest, intrusive thoughts, nightmares, hypervigilance, sleep disturbances and flashbacks of past trauma. For most patients, onset occurs within a few months of the traumatic event but ~25% of patients experience a delay in onset of 6+ months. One third of patients recover within 1 year. PTSD is commonly chronic with one third of patients still symptomatic 10 years after exposure to trauma.

About 15-30% of PTSD patients suffer dissociative PTSD—a severe subtype due to early/repetitive trauma. Dissociative PTSD is also characterised by a higher level of comorbid psychiatric disorders and increased suicidality (including ideation, plans, and attempts).

The highest prevalence rates of PTSD have been found in general adult population in the United States and Canada. In 2012 the lifetime prevalence of PTSD in US and Canada ranged from 6.1 to 9.2%, with one-year prevalence rates of 3.5 to 4.7%. In Europe, the one-year prevalence of PTSD in 2016 was about 1.3%.

Pathophysiology of PTSD

The pathophysiology of PTSD remains to be established although several theories have been advanced referring to the most common pathways associated to human/mammalians behaviours. In reality this remains highly speculative, and it is illustrated by the large variety of pre-clinical models and the lack of consistency of efficacy within a single therapeutic class. Indeed, although almost all SSRIs have been tested only two have emerged in the clinical guidelines. The pathophysiology of PTSD may involve dysfunction of several brain structures, particularly the amygdala, locus coeruleus, and hippocampus, prefrontal and anterior cingulate cortex, as well as noradrenergic system and hypothalamic-pituitary-adrenal (HPA) axis. Acute and repeated stressors disrupt frontal-cortical control over limbic-striatal circuits which constitute the brain stress circuit, increase mesolimbic dopaminergic transmission, and increase prefrontal cortex noradrenaline and serotonin transmission. Although such stress induced these brain modifications in all individuals, only a limited number will develop PTSD.

Serotonin regulates sleep, appetite, sexual behaviour, aggression/impulsivity, motor function, analgesia, and neuroendocrine functions. Serotoninergic neurons of the brain stem region dorsal raphe mediate anxiogenic effects while serotoninergic neurons from the median raphe mediate anxiolytic effects, facilitate extinction, and suppress encoding of learned associations. Chronic exposure to stressors induces upregulation of serotonin type 2 receptors and downregulation of serotonin type 1A receptors, resulting in increased stress responses.

In PTSD serotonin concentrations are decreased in the brain stem regions dorsal and median raphes, with secondary dynamic disturbance between their areas of projection, amygdala and hippocampus. Decreased serum concentrations of serotonin and altered responsiveness to CNS serotonergic paths have been shown in PTSD patients. In addition, alterations in serotonin transmission may contribute to symptoms of PTSD including hypervigilance, increased startle, impulsivity, and intrusive memories, though the exact roles and mechanisms remain uncertain.

Dopamine is widely accepted as a major neurotransmitter. Combat stress in human has adverse effects on the circuit between hippocampus (memory recall), amygdala (fear) and prefrontal cortex (high thought, self-judgement, and behaviour choices), impacts normal dopaminergic function and reduces the ability to cope with stress. Low dopamine function has been associated with increased risk for PTSD: many polymorphic genes, particularly the genetic determinants of low dopamine function associate with a predisposition to PTSD. However there is no evidence of antipsychotics efficacy, as further detailed below, and none is recommended as first or second line or even third line for treating PTSD. PTSD is also associated to an increased content of CNS in corticotropin-releasing factor (CRF) concentrations, as well as a decrease in catecholamines (incl. noradrenaline). But here again none of the noradrenergic mediated antidepressants is recommended by the most recent guidelines to treat PTSD.

Treatment of PTSD

Preferred treatment according to clinical guidelines are cognitive behavioural therapy (CBT), cognitive processing therapy (CPT), cognitive therapy (CT) and prolonged exposure therapy (PE). This puts in perspective the limited efficacy of pharmacotherapies.

In terms of medications, two selective serotonergic reuptake inhibitors (SSRIs), sertraline and paroxetine, and one serotonin norepinephrine reuptake inhibitors (SNRIs), venlafaxine, have been recommended for the treatment of PTSD by the US Department of Veterans Affairs (VA/DoD). This guideline suggests that all antidepressants within a class, SSRI or SNRI, cannot be considered equivalent for the treatment of PTSD. Furthermore, none of tricyclic antidepressants (TCA) is recommended in the treatment of PTSD, as a recent systematic review found that the evidence concerning a potential benefit of TCAs in PTSD was of low certainty. This is consistent with the fact that venlafaxine has a 30-fold higher affinity for the reuptake inhibition of serotonin compared to norepinephrine. At lower doses, venlafaxine primarily inhibits serotonin reuptake, and at higher doses, it inhibits both serotonin and norepinephrine reuptake. Therefore, it is more potent as a serotonin reuptake inhibitor than a norepinephrine reuptake inhibitor Also, one may consider that the SSRI activity is critical for the efficacy of venlafaxine.

As concerns antipsychotics, the Cochrane review found no evidence of benefit for the number of participants who improved, compared to placebo, based on very low-certainty evidence. The VA/DoD does not recommend for or against antipsychotics including olanzapine or quetiapine, based on insufficient evidence, but recommends against risperidone in PTSD.

No recommendation is given by the VA/DoD regarding $2^{nd}$-line therapies. A large-scale multi-site trial of risperidone as an adjunctive agent for SSRI poor/partial responders showed that there was no benefit (in comparison with a placebo group) for adjunctive use of this agent.

It is very surprising to observe the lack of efficacy of antipsychotics while they are primarily targeting the Dopamine receptors (D1 and/or D2) while it is considered as a critical pathway for the pathophysiology of PTSD.

Carpipramine

Carpipramine, or 5-[3-(4-carbamoyl-4-piperidinopiperodino)-1-propyl-10,11-dihydrodibenz[b,f]azepine, is an antipsychotic drug that belongs to the iminodibenzyl class, indicated for the treatment of schizophrenia.

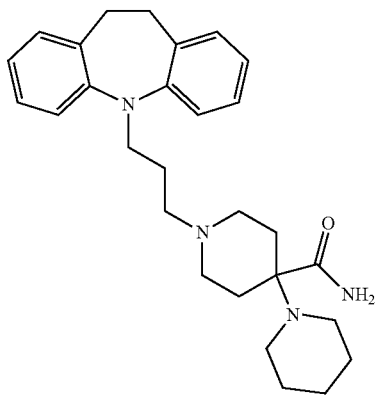 [SMILES: NC(=O)C1(N2CCCCC2)CCN(CCCN2c3ccccc3CCc3ccccc32)CC1]

This drug possesses several kinds of effects: disinhibitory, antidelusional and neuroleptic. It has been evaluated in several indications:

Schizophrenia: Carpipramine is a potent dopamine antagonist which block alpha 1- and alpha 2-adrenoceptors in the brain. A systematic literature review and meta-analysis concluded that carpipramine, which is classified as a second-generation antipsychotic, has efficacy and safety outcomes comparable to first-generation antipsychotics. It was found to be effective in patients with negative symptoms, but could worsen positive symptoms.

Depression: although it has a chemical structure close to imipramine, carpipramine was found to have less effect than tricyclic antidepressants against melancholy, and it is not considered an antidepressant. It possesses antagonist properties with respect to serotonin (5-HT2) receptors, but studies on the metabolic fate and effects of carpipramine on serotonin levels in the brain found that it did not modify serotonin uptake, which supports the idea that the efficacy is not mediated by the serotoninergic pathway. Opioid dependence: carpipramine was found to be effective against apathy in patients treated for opioid dependence. Neurotic disorder: carpipramine was found to be effective against symptom patterns consisting essentially of asthenia, inhibition and psychomotor impairment, to raise the level of activity, and to stimulate enthusiasm and relational activity in patients with neurosis.

Overall, the action of carpipramine is quite complex, but its effect is predominantly mediated by the dopaminergic pathway, as for all antipsychotics. It is classified as a second-generation antipsychotic while its effects are more similar to first-generation antipsychotics. It appears to have a dual action: stimulating at low doses and sedative at high doses.

The mechanism of action of carpipramine, alongside two iminodibenzyl antipsychotic drugs, was elucidated in an animal by Setogushi et al, 1985. They all accelerated the accumulation of the dopamine (DA) metabolites, homovanillic acid (HVA) and 3,4-dihydroxyphenylacetic acid (DOPAC), in the striatum and nucleus accumbens of the rat brain.

All three drugs showed high affinity for DA receptors labelled by [$^3$H]haloperidol and [$^3$H]ADTN in the rat striatum in vitro, with the order of potency Y-516 greater than clocapramine greater than carpipramine. All accelerated the accumulation of the norepinephrine metabolite, 3-methoxy-4-hydroxyphenylglycol (MHPG), in mouse brain. They showed high affinity for alpha 1-.adrenoceptors labelled by [$^3$H]WB 4101 and for alpha 2-adrenoceptors labelled by [$^3$H]clonidine in the rat cerebral cortex in vitro. The above results indicated that these drugs are potent dopamine antagonists which block alpha 1- and alpha 2-adrenoceptors in the brain.

Cariprazine also binds with alpha-1 adrenoreceptors, but with low affinity). One study specifically investigated whether alpha-2 adrenergic receptors were involved in cariprazine's effects and found no evidence of such involvement. More generally, carpipramine has a unique structure presenting similarities with both tricyclics' chemical structure, linked to antidepressant activity, and butyrophenone, which is linked to its antipsychotic effects. However, as previously mentioned in our submission, studies on the metabolic fate and effects of carpipramine on serotonin levels in the brain found that it did not modify serotonin uptake, which supports the idea that the efficacy is not mediated by the serotoninergic pathway as for products known to be partially effective on PTSD.

A review on the receptor binding profiles of antipsychotics (not including carpipramine) shows that there is large variability in profiles of antipsychotics, and it is difficult to predict clinical effects from receptor binding profiles as they are all unique. Patients may respond to one or the other antipsychotics, and it is unpredictable to which antipsychotic a given patient will respond.

The efficacy of carpipramine discovered by serendipity and confirmed in animal models, is a novelty and could not be predicted from available pharmacological, clinical knowledge. It could not be extrapolated from active therapies on PTSD and failure of risperidone in second line population suffering of PTSD suggested antipsychotics are inappropriate therapy for this indication.

In anatomical terms, PTSD is characterized by smaller hippocampal volume, which may predispose individuals to stronger fear perceptions and persistent conditioned psycho-emotional responses. In terms of neurochemistry, the differentiation is quite difficult: there are abnormalities related to dopamine, serotonin and norepinephrine in all diseases. However, although antipsychotics, which are dopamine antagonists, were found to be effective against schizophrenia and BD, they are not effective in PTSD (see previous submission for references). Hypocortisolism appears to be more consistently observed in PTSD, although it is not a definitive marker: several studies report lower basal cortisol levels in PTSD patients, while bipolar disorder patients may exhibit both hyper- and hypocortisolism, and cortisol levels are rather elevated in schizophrenia patients.

There is currently no published study concerning carpipramine in PTSD. It may also be noted that although carpipramine present similarities with antipsychotics, the effects of antipsychotics in PTSD remain largely unknown, as mentioned above, and they are not recommended for the pharmacological treatment of PTSD Carpipramine received a marketing authorization in France in 1977, and it was commercialized under the brand name Prazinil, until its authorization was withdrawn in 2014. The approved dosage was 50 to 400 mg per day. It is available in Japan, under the brand name Defekton. It has never been available in other countries, including the US. It has been found that carpipramine possesses efficacy in the treatment of PTSD in after failure of pharmacotherapy with an antidepressant (AD), an antipsychotic (AP), or both.

DETAILED DESCRIPTION OF THE INVENTION

The method involves identifying or selecting subjects who have PTSD and administering the treatment to these subjects. The subject can be male or female. The Diagnostic and Statistical Manual, Fifth edition, (DSM-V) classifies PTSD as a trauma- and stressor-related disorder. The criteria for diagnosis of PTSD include presence of a stressor (required), intrusion symptoms (required), avoidance of trauma-related stimuli (required), negative alterations in cognitions and mood (required), alterations in arousal and reactivity, with a duration of more than 1 month and functional significance.

A subject can be selected that has PTSD as defined by the DSM-V criteria. The subject can be an adult or a child. The subject may have previously failed to respond to an antidepressant, including but not limited to paroxetine, sertraline and venlafaxine, and/or an antipsychotic, including but not limited to risperidone, quetiapine, aripiprazole and olanzapine, used as monotherapy or combined.

Most preferably, the method includes the use of carpipramine or a pharmaceutically acceptable salt thereof for the preparation of a medicament for the treatment of PTSD. In this most preferred embodiment, carpipramine is the sole active ingredient in the treatment, and is not combined with other medications.

Another embodiment of the method includes the use of carpipramine or a pharmaceutically acceptable salt thereof for the preparation of a medicament for the treatment of antidepressant and antipsychotic-resistant PTSD in combination with an antidepressant, including but not limited to paroxetine, sertraline and venlafaxine.

It is also within the scope of the invention to provide liquid formulations, in particular aqueous formulations, for oral administration. A further route of administration is by intravenous or intramuscular injection in a liquid carrier such as physiological saline.

The term "therapeutically effective amount" as defined in this invention means an amount of the compound which is effective in treating a patient for PTSD.

PTSD may be treated by administering carpipramine to a subject in a dose ranging from about 50 to 400 mg per day.

It is also within the scope of the invention to provide extended-release formulations, which may release a therapeutically effective amount of carpipramine in the human body over several days, weeks or months. The following examples are intended for illustrative purposes only and are not meant to limit the invention in any manner.

EXAMPLES

Example 1: Social Isolation Experience in Mice—an Experiment Based on the Socially Isolated Mice Model was Performed Methods Socially isolated mice express a decrease in corticolimbic allopregnanolone levels that is associated with an enhancement of contextual fear responses and impaired fear extinction. Social isolation can be seen as a prolonged stress that is often associated with a precipitating traumatic event, which leads to maladaptive post-stress adaptations and emergence of PTSD in patients. Thus, social isolation is considered to offer a suitable model to study vulnerability to PTSD.

Ten (10) male Swiss-Webster mice were socially isolated for a period of 4 weeks, in individual cages, according to a protocol proposed by Pinna et al.

Day 0—Training Test. During the training, mice were placed into the training chamber and allowed to explore it for 2 min. After this time, they received a conditioned stimulus (acoustic tone, 30 seconds, 85 dB) co-terminated with an unconditioned stimulus (electric foot shock, 2 s, 0.5 mA). This was repeated three times every 2 min. After the last stimuli, mice were allowed to explore the context for an additional minute before removal from the training chamber (total of 8 min).

Day 1—Contextual Test. Twenty-four hours after training, the mice were placed in the contextual cage, and freezing behavior was measured for 5 min without tone or foot shock presentation. Freezing was defined by the absence of any movement except for those related to respiration while the animal was in a stereotypical crouching posture. Freezing time in a index of fear response.

Days 2-5—Extinction Test. For contextual extinction experiments, mice were placed in the contextual cage for periods of 5 min over 4 consecutive days starting 24 h after the contextual test, and freezing behavior was measured.

After the contextual test, 5 mice received a dose of 10 mg/kg of carpipramine subcutaneously. Injections were repeated on days 2 to 4.

Results

The mean duration of freezing on day 1 was 117 seconds (SE: 6.6) in the treated group and 123 seconds (SE: 8.7) in the control group. The magnitude of reduction was significantly greater in the treated group. The duration of freezing decreased to 18 seconds (SE: 6.5) in the treated group and 43 seconds (SE: 5.0) in the control group ($p<0.01$).

TABLE 1

| | Change in duration of freezing (mean ± standard error of the mean) | | | | |
|---|---|---|---|---|---|
| | Treated mice | | Untreated mice | | p- |
| Day | Mean | SE | Mean | SE | value |
| 2 | −76 | 6.4 | −37 | 7.6 | <0.01 |
| 3 | −93 | 7.0 | −70 | 7.3 | <0.01 |

TABLE 1-continued

Change in duration of freezing (mean ± standard error of the mean)

| Day | Treated mice Mean | Treated mice SE | Untreated mice Mean | Untreated mice SE | p-value |
|---|---|---|---|---|---|
| 4 | −98 | 6.6 | −78 | 7.3 | <0.01 |
| 5 | −99 | 6.2 | −80 | 7.3 | <0.01 |

Example 2: Forced Swim Test to Evaluate the Effects of Carpipramine on Depressive Like Behaviors in Rats An experiment was conducted to assess the impact of carpipramine compared to paroxetine and olanzapine on depressive-like behaviors following trauma experience in mice using the forced swim test.

Methods

The experiment included 30 mice, randomly allocated to 3 groups treated with carpipramine, paroxetine and olanzapine.

The mice were socially isolated for a period of 3 weeks in individual cages, with a 12-hour light/dark cycle. They had access to food and water at libitum.

On day 21, a pre-test was performed. Cylindrical tanks were filled with water (approximately 25° C.) to a depth that prevents mice from touching the bottom. Each mouse was placed in a water-filled cylinder for 6 minutes. If the mouse was swimming or struggling after 6 minutes, it was gently submerged, so that it would struggle under the surface for up to 20 seconds. After this time elapsed, the mouse was removed from the container and placed in a transient drying cage with a heat lamp above it and a heat pad under it. The mice were closely and continuously monitored while recovering in this cage.

The mice were then isolated for a period of 2 weeks in the same conditions as before the pre-test. They were treated during that period with one of three randomly allocated treatments:

Carpipramine, 5 mg/kg, subcutaneous, daily
Paroxetine, 1 mg/kg, subcutaneous, daily
Olanzapine, 0.3 mg/kg, subcutaneous, daily The test was performed on day 36. Mice were placed again in water-filled cylinders for 6 minutes, and then moved to a drying cage.

The behaviour of mice was coded over the minutes 3 to 6 of each test, in 3 categories: immobile, struggling and swimming. The time associated with each type of behaviour was recorded. A reduction in immobility time is considered predictive of antidepressant properties.

Results

The reduction in immobility time in the carpipramine group was greater than in the paroxetine group (p=0.16, not statistically significant), and in the olanzapine group (p<0.001).

TABLE 1

Change in immobility time compared to pre-test

| Treatment group | Number of mice | Mean change in immobility time (seconds) | 95% confidence interval |
|---|---|---|---|
| Carpipramine | 10 | −104.3 | [−135.9, −72.7] |
| Paroxetine | 10 | −82.2 | [−112.9, −51.4] |
| Olanzapine | 10 | +19.5 | [−9.2, +48.1] |

Conclusion

This experiment suggests an efficacy of carpipramine at least similar or possibly higher to paroxetine, and significantly higher than the antipsychotic olanzapine, against depressive-like behaviour, in a context involving prior exposure to a trauma. These results are unexpected for an antipsychotic.

Example 3: Comparative Effects of Carpipramine, Sertraline, Amitriptyline and Quetiapine in Rats Subjected to Psychosocial Stress An experiment was conducted to assess the effects of carpipramine, sertraline, amitriptyline and quetiapine in rates subjected to psychosocial stress (predator exposure and housing instability) against PTSD-like behaviours, based on a protocol adapted from Zoladz et al (2012).

Methods

Adult male Sprague-Dawley rats were used in all experiments. Fifty (50) rats were pair-housed on a 12-h light/dark schedule in cages with free access to food and water.

Following a 1-week acclimation phase, they were given two 1-h cat exposures, separated by 10 days, in conjunction with daily social stress in the form of randomized housing. During each of the two cat exposures, rats were placed in a perforated wedge-shaped Plexiglas enclosure. The rats, still immobilized within the Plexiglas enclosure, were taken to the cat housing room where they were placed in a metal cage with an adult female cat for 1 hour. The Plexiglas enclosure prevented any physical contact between the cat and rats, but enabled the rats to be exposed to all non-tactile sensory stimuli associated with the cat. The two cat exposures were separated by 10 days, with the first exposure taking place during the light cycle, and the second exposure taking place during the dark cycle. Beginning on the day of the first cat exposure, rats were exposed to unstable housing conditions for the next 31 days. They were housed two rats per cage, with their cohort pair combination changed on a daily basis during the entire 31-day stress period.

The rats were randomly assigned to 5 groups of 10, treated with carpipramine, sertraline, amitriptyline, quetiapine and saline. The treatments were administered as daily intraperitoneal injections over 21 days, starting from the day following the second cat exposure. Daily doses were as following:

Carpipramine: 5 mg/kg
Sertraline: 5 mg/kg
Amitriptyline: 2 mg/kg
Quetiapine: 10 mg/kg Since a major component of PTSD is the persistent memory of a traumatic experience, a method with which to measure a rat's memory for the cat exposure experiences was used. Thus, rats were given a predator-based form of fear conditioning. The rats were placed in a chamber for 3 minutes immediately prior to each of the two cat exposures.

The chamber consisted of two aluminium sides, an aluminium ceiling and clear Plexiglas on the front and back walls and speaker on one wall. A 74 dB, 2500 Hz tone was presented during the last 30 seconds of each chamber exposure. Three weeks following the second cat exposure, the rats were tested for their conditioned fear memory by assessing their freezing response (degree of immobility) when they were returned to the chamber and exposed to the tone. Rats were placed in the chamber, which had been previously paired with the 2 cat exposures, for 5 minutes (context memory test). One hour later, the rats were placed in the chamber with aluminium sides and ceiling, with a 74 dB, 2500 Hz tone presented during the last 3 minutes of the exposure (cue memory test). Immobility in the chambers was operationally defined as continuous periods of inactivity lasting at least 7 seconds. For the cue memory test, the percentage of immobile time was measured during the last 3 minutes (i.e. during the tone).

Twenty-four hours after fear conditioning memory testing, the rats were placed on an elevated plus maze (EPM) for 5 minutes. The EPM is a routine test of anxiety in rodents and consists of two open arms and two closed arms of same size (11 cm by 50 cm) that intersect each other to form the shape of a plus sign. At the beginning of each trial, the rats were placed in the intersection area of the EPM, facing one of the open arms. The primary dependent measures of interest were the amount of time rats spent in the open arms and their overall ambulations.

Results

The results of tests are shown in the table below. The percentage of immobility time in the context memory test and cure memory test were significantly reduced with carpipramine compared to amitriptyline, quetiapine and saline. A greater reduction was also found vs. sertraline in the percentage of immobility time during the context memory test (p<0.05). In the EPM test, the carpipramine group spent more time in open arms, compared to other groups, suggesting lower anxiety. The difference was statistically significant compared to saline (p=0.02) but not vs. sertraline, amitriptyline and quetiapine (p=0.27, p=0.09 and p=0.017 respectively).

TABLE 2

Results of context memory test, cue memory test and elevated plus maze (EPM) test following repeated exposure to a predator and chronic stress caused by housing instability Context memory

| | % immobility time | | |
|---|---|---|---|
| Treatment group | Mean | SEM | p-value* |
| Carpipramine | 22.3 | 5.3 | |
| Sertraline | 37.1 | 7.1 | 0.05 |
| Amitriptyline | 64.5 | 9.2 | <0.01 |
| Quetiapine | 53.4 | 9.6 | <0.01 |
| Saline | 62.7 | 8.8 | <0.01 |

Cue memory (during tone)

| | % immobility time | | |
|---|---|---|---|
| | Mean | SEM | p-value |
| Carpipramine | 14.6 | 8.5 | |
| Sertraline | 25.7 | 10.7 | 0.21 |
| Amitriptyline | 42.7 | 10.3 | 0.03 |
| Quetiapine | 39.3 | 11.2 | 0.04 |
| Saline | 45.1 | 8.3 | <0.01 |

TABLE 2-continued

Results of context memory test, cue memory test and elevated plus maze (EPM) test following repeated exposure to a predator and chronic stress caused by housing instability EPM-Open arm exploration

| | % time in open arm | | |
|---|---|---|---|
| | Mean | SEM | p-value |
| Carpipramine | 42.1 | 10.3 | |
| Sertraline | 32.5 | 11.1 | 0.26 |
| Amitriptyline | 20.6 | 11.9 | 0.09 |
| Quetiapine | 28.7 | 9.6 | 0.17 |
| Saline | 16.3 | 7.2 | 0.02 |

*p-values are provided for one-sided tests of carpipramine compared to other treatments.

Conclusion

The comparison of carpipramine to saline demonstrated a significant effect of carpipramine in alleviating traumatic memory expression and anxiety in rats exposed to a traumatic experience. Compared to quetiapine and amitriptyline, carpipramine appeared to significant alleviate traumatic memory expression. Compared to sertraline, tests results were consistently better with carpipramine, with a significantly greater effect in the context memory test. This suggests potent effects of carpipramine in PTSD, greater than the effects of quetiapine and amitriptyline, and at worst similar and possibly greater than the effects of sertraline. These results were fully unexpected.

Example 4

A 27-year-old male was referred to a psychiatrist by his general practitioner as he suffered from anxiety, sleep problems and nightmares. The subject had a history of anxiety disorders and had been involved in a serious car accident 8 months earlier, causing the death of his partner. He was on leave from his position as a teacher. The subject was diagnosed with PTSD and a cognitive behavioural therapy was initiated. As the subject was strongly inhibited due to anxiety, a prescription of oral carpipramine, 100 mg/daily, was also made. All PTSD symptoms improved markedly after the initiation of carpipramine treatment.

Example 5

A French female patient was followed by a psychiatrist due to depression symptoms, including sadness, feeling of hopelessness, apathy and anxiety. The patient was initially treated with fluoxetine, which lead to improvement in most symptoms, but anxiety persisted. Fluoxetine was stopped after 6 months. About one year later, the depression symptoms recurred, alongside with auditory hallucinations. The patient was then 32 years old. A treatment for schizophrenia was initiated, with risperidone and psychological therapy, leading to modest improvement. Three months later, fluoxetine was reintroduced alongside with risperidone. The patient's mood improved, but she still suffered from anxiety and auditory hallucinations. After 6 weeks with the combination of risperidone and fluoxetine, risperidone was replaced by carpipramine (150 mg/day). The patient entered in remission two weeks later. Subsequent exchanges with the psychologist later established a link between symptoms and a history of sexual violence, which suggested that the patient had in fact been suffering from PTSD.

Example 6

A 28-year-old male veteran presented to a psychiatrist with major depressive disorder (sadness, irritability, poor concentration, suicidal thoughts). The patient was initially treated with sertraline and showed no improvement. New symptoms emerged, including nightmares and anxiety. The medication was then switched to venlafaxine after 2 months. This resulted in some improvement, but severe symptoms persisted. Olanzapine was subsequently added, and the patient entered in remission. Three months later, the patient relapsed, and was experiencing anxiety symptoms, nightmares and mildly depressed mood. The relapse was treated with carpipramine (initiated at 200 mg/day), which led to remission after 4 weeks of treatment. The patient's condition was stable for about 3 years. The symptoms (anxiety, nightmares, moderately depressed mood) reappeared after that time, together with hallucinations and flashbacks of combat. The diagnostic of PTSD was then established. Carpipramine (200 mg/day) was prescribed again, following the previous experience. The patient entered remission after 3 weeks of treatment.

Although embodiments and examples of the invention have been shown and described, it is to be understood that various modifications, substitutions, and rearrangements of parts, components, steps, as well as other uses, shapes, construction, and design of this system can be made by those skilled in the art without departing from the novel spirit and scope of this invention.

The invention claimed is:

1. A method of treating post-traumatic stress disorder (PTSD) in a subject, wherein the method comprises administering to the subject in need of treatment a therapeutically effective amount of carpipramine or a pharmaceutically acceptable salt thereof, where the carpipramine or its corresponding salt is the sole active ingredient.

2. The method according to claim 1, wherein the administration is oral.

3. The method according to claim 1, wherein the administration is intravenous.

4. The method according to claim 1, wherein the administration is intramuscular.

5. The method according to claim 1, wherein the amount administered is 50 to 400 mg per day.

6. The method according to claim 1, wherein the treatment is administered daily.

7. The method according to claim 1, wherein the treatment is administered in an extended-release formulation, lasting over several days, weeks or months.

8. The method according to claim 1, wherein the subject was never previously treated with an antidepressant or antipsychotic.

9. The method according to claim 1, wherein the subject previously failed to respond to treatment with an antidepressant selected from the group consisting of sertraline, paroxetine and venlafaxine.

10. The method according to claim 1 wherein the subject previously failed to respond to treatment with an antipsychotic selected from the group consisting of olanzapine, quetiapine, and aripiprazole.

11. The method according to claim 1 wherein the subject previously failed to respond to treatment with an antidepressant selected from the group consisting of sertraline, paroxetine and venlafaxine, and an antipsychotic selected from the group consisting of olanzapine, quetiapine, and aripiprazole administered sequentially or concomitantly.

* * * * *